(12) United States Patent
Azuma et al.

(10) Patent No.: US 7,534,443 B1
(45) Date of Patent: May 19, 2009

(54) PREPARATIONS FOR IMMUNOTHERAPY FOR CANCER HAVING BACTERIAL SOMATIC CONSTITUENT AS THE ACTIVE INGREDIENT

(75) Inventors: Ichiro Azuma, 3-2, Makomanaikami-machi 5-chome, Minami-ku, Sapporo-shi, Hokkaido (JP); Norio Hamamatsu, Kawanishi (JP); Toshio Fujinaga, Ibaraki (JP)

(73) Assignees: Ichiro Azuma, Hokkaido (JP); Akira Hayashi, Osaka-fu (JP); Dainippon Sumitomo Pharma Co., Ltd., Osaka-fu (JP)

( * ) Notice: Subject to any disclaimer, the term of this patent is extended or adjusted under 35 U.S.C. 154(b) by 0 days.

(21) Appl. No.: 09/743,750

(22) PCT Filed: Jul. 16, 1999

(86) PCT No.: PCT/JP99/03837

§ 371 (c)(1),
(2), (4) Date: Mar. 26, 2001

(87) PCT Pub. No.: WO00/03724

PCT Pub. Date: Jan. 27, 2000

(30) Foreign Application Priority Data

| Jul. 16, 1998 | (JP) | 10-202366 |
| Aug. 21, 1998 | (JP) | 10-236148 |
| Aug. 21, 1998 | (JP) | 10-236163 |
| Aug. 21, 1998 | (JP) | 10-236164 |

(51) Int. Cl.
*A61K 39/04* (2006.01)
*A61K 45/00* (2006.01)
*A61K 39/38* (2006.01)
*A61K 39/02* (2006.01)

(52) U.S. Cl. ............ 424/248.1; 424/283.1; 424/184.1; 424/234.1

(58) Field of Classification Search ............ 424/88, 424/95, 21; 514/885, 937, 938, 21
See application file for complete search history.

(56) References Cited

U.S. PATENT DOCUMENTS

| 4,436,728 | A |   | 3/1984  | Ribi et al. |
| 4,543,253 | A | * | 9/1985  | Yamamura et al. ............ 514/21 |
| 4,877,611 | A | * | 10/1989 | Cantrell .................... 424/277.1 |
| 6,416,740 | B1| * | 7/2002  | Unger ......................... 424/52 |
| 6,451,325 | B1| * | 9/2002  | Van Nest et al. ......... 424/283.1 |
| 6,593,096 | B1|   | 7/2003  | Hayashi et al. |
| 7,273,602 | B2|   | 9/2007  | Hayashi et al. |
| 2003/0108527 | A1 | | 6/2003 | Seya et al. |
| 2007/0172499 | A1 | | 7/2007 | Hayashi et al. |

FOREIGN PATENT DOCUMENTS

| JP | 54-23313 A  | 3/1979 |
| JP | 60-1133 A   | 1/1985 |
| JP | 60-120817 A | 6/1985 |
| WO | 96/14871 A1 | 5/1996 |

OTHER PUBLICATIONS

Yarkoni et al, Infection and Immunity, 28(3):881-886 (1980).*
Yarkoni et al (Infection and Immunity, 28(3):881-886 (1980)).*
Zbar et al (Journal of National Cancer Institute, Vo. 48, No. 3, p. 831-835).*
Yarkoni et al (Infection and Immunity, 28(3):881-886 (1980)).*
Zbar et al (Journal of National Cancer Institute, 1972, vol. 48, No. 3, p. 831-835).*

* cited by examiner

*Primary Examiner*—Robert B. Mondesi
*Assistant Examiner*—Vanessa L. Ford
(74) *Attorney, Agent, or Firm*—Birch, Stewart, Kolasch & Birch, LLP.

(57) ABSTRACT

An oil-in-water emulsion that comprise a bacterial component as an active ingredient as well as essentially an oil, surfactant, and a stabilizer, and that can be used as an agent for immunotherapy, and the preparation therefor are provided.

4 Claims, 8 Drawing Sheets

×400   0  50  100 μm

×400   0  50  100 μm

×400  0 50 100 μm

×400  0 50 100 μm

×400    0  50  100 μm

×400    0  50  100 μm

PREPARATIONS FOR IMMUNOTHERAPY FOR CANCER HAVING BACTERIAL SOMATIC CONSTITUENT AS THE ACTIVE INGREDIENT

This application is the national phase under 35 U.S.C. § 371 of PCT International Application No. PCT/JP99/03837 which has an International filing date of Jul. 16, 1999, which designated the United States of America.

TECHNICAL FIELD

The invention relates to an oil-in-water emulsion capable of using for immunotherapy for cancers, which comprises a bacterial component having an immunopotentiating activity as an active ingredient, as well as essentially an oil, a surfactant, and a stabilizer, and to a preparation therefor.

BACKGROUND ART

It has been acknowledged that dead bacteria, and bacterial components such as a cell wall skeleton integrant (hereinafter, it is abbreviated as CWS), muramyl dipeptide (MDP), a lipopolysaccaride (LPS), mannan and glucan of bacteria, and a derivative thereof (it may include substances produced by recombinant DNA technique) have an immunopotentiating activity, and exhibits an anti-tumor effect for example in experimental cancer cell lines and in immunotherapy for human cancers. Further, it has been acknowledged that, when formulated into an oil-in-water emulsion by dispersing it in an oil with a dispersing or emulsifying device such as a homogenizer, and besides by emulsifying the dispersion in a surfactant solution, the bacterial components exhibit a better antitumor and infection-preventing effect via an immunopotentiating activity (Cancer Res., 33, 2187-2195 (1973), J. Nat. Cancer Inst., 48, 831-835 (1972), J. Bacteriol., 94, 1736-1745 (1967), Gann, 69, 619-626 (1978), J. Bacteriol., 92, 869-879 (1966)).

However, although oil-in-water emulsions as mentioned above have gained a good reputation in utility (Proc. Japan Acad., 70, Ser. B205-209 (1994); Proc. Japan Acad., 74, Ser. B20550-55 (1998)), there have been any problem that the emulsions are prohibited to be constantly, supplied to market since it is difficult, due to the following reasons, that they are commercially produced. The present invention was developed to overcome the various drawbacks that make their commercial production difficult, and resolve the problem as mentioned above. Such drawbacks and means for resolving the same are discussed as shown below.

In general, an oil-in-water emulsion is liable to be largely altered with the time course, resulting in separation between oil and aqueous phases. Thus, to stabilize an emulsion, various measures have been taken such as (1) making particles, (2) reducing the difference in specific gravity between a dispersion medium and a dispersoid, and (3) elevating the viscosity of a dispersion medium with addition of a high-molecular substance, and the like. However, all of them merely extend a period of time required for the alteration, and finally lead to the separation between oil and aqueous phases Particularly, an oil-in-water emulsion comprising a bacterial component as an active ingredient was shown to be unstable due to the included CWS, thus generating insoluble aggregations in a few days, and therefore, there was no means but the preparation just before use in order to prepare an oil-in-water emulsion. To cope with this point, a sugar alcohol and a saccharide was tried in formulations by lyophilization (Japanese Patent Publication (kokoku) No. 1291/1988).

However, the formulations in the state of the art demonstrated large changes in average particle diameter and particle size distribution immediately after lyophilization and as short as one month after the preservation, and therefore, any emulsions have not accomplished significant, improvement in stability that provides practical use.

DISCLOSURE OF THE INVENTION

As a result of our studies, we found that addition of a suitable stabilizer to an oil-in-water emulsion formulation comprising a bacterial component as an active ingredient enables stable lyophilization and improvement in stability of the formulation. It means that even when re-dispersed in a suitable dispersion solvent such as water, a lyophilized formulation from an oil-in-water emulsion according to the present invention retains its average particle diameter, its particle diameter distribution, or its turbidity (relative absorbance) similarly to those prior to the lyophilization. Further, even when dispersed in a suitable dispersion solvent such as water after preservation for a long period, a lyophilized formulation from an oil-in-water emulsion according to the present invention retains its average particle diameter, its particle diameter distribution, or its turbidity (relative absorbance) similarly to those prior to the lyophilization.

Thus, the first solution of the problem according to the present invention is summarized by;

(1) A stable lyophilized formulation obtainable by lyophilization of an oil-in-water emulsion comprising a bacterial component, an oil, a surfactant, and a stabilizer, which emulsion is characterized in that:

(a) the bacterial component is encapsulated in an oil droplet;

(b) the oil droplets are dispersed with a single peak of particle diameter distribution in the aqueous solution; and (c) the particle diameter distribution of the oil droplets and turbidity in the aqueous solution are not largely changed before and after lyophilization:

(2) The stable lyophilized formulation according to the above (1), which is formed into an aqueous solution, of which the turbidity is changed by 50% or less compared to that of an aqueous solution before lyophilization:

(3) The stable lyophilized formulation according to the above (1) or (2), wherein the bacterial component is a BCG-CWS, and the oil is squalane:

(4) The stable lyophilized formulation according to any one of the above (1) to (3), wherein the stabilizer is an amino acid or urea:

(5) The stable lyophilized formulation according to any one of the above (1) to (3), wherein the stabilizer is glycine:

(6) A process for preparation of a stable lyophilized formulation, which comprises lyophilizing an oil-in-water emulsion comprising a bacterial component, an oil, a surfactant, and a stabilizer, which emulsion is characterized in that:

(a) the bacterial component is encapsulated in an oil droplet;

(b) the oil droplets are dispersed with a single peak of particle diameter distribution in the aqueous solution; and (c) the particle diameter distribution of the oil droplets and turbidity in the aqueous solution are not largely changed before and after lyophilization:

(7) The process for preparation of a stable lyophilized formulation according to the above (6), which formulation is formed into an aqueous solution, of which the turbidity is changed by 50% or less compared to that of an aqueous solution before lyophilization:

(8) The process for preparation of a stable lyophilized formulation according to the above (6) or (7), wherein the bacterial component is a BCG-CWS, and the oil is squalane:

(9) The process for preparation of a stable lyophilized formulation according to any one of the above (6) to (8), wherein the stabilizer is an amino acid or urea: and

(10) The process for preparation of a stable lyophilized formulation according to any one of the above (6) to (8), wherein the stabilizer is glycine.

Another drawback that makes it difficult to produce commercially an oil-in-water emulsion comprising a bacterial component as an active ingredient is that the production of the emulsion in a large scale while retaining an immunopotentiating activity is extremely hard.

In other words, a process for preparing an oil-in-water emulsion was first tested to establish a commercial preparation process, which comprises dispersing a crude material of BCG-CWS in an isotonic solution, then adding an oil thereto, dispersing the mixture, adding a surfactant thereto, and emulsifying the mixture so that any difficulty in dispersing homogeneously the bacterial component in the oil caused by use of the oil in a quite small amount relative to water is eliminated, which process was designed from the well-known process for formulating an oil-in-water emulsion just before use (J. Nat. Cancer Inst. 48, 831-835 (1972), J. Bacteriol, 92, 869-879 (1966), Gann, 69, 619-626 (1978)). However, the first trial formulation obtained by the preparation mentioned above demonstrated to be biologically inactivated in terms of inhibitory effect on proliferation of tumor in mice, although its particle size distribution and its condition observed under micrography were nearly equal to those of the known formulation to be prepared just before use. Further, a formulation without an oil also demonstrated biologically inactivated.

As discussed above, any utility in the biological aspect of a formulation comprising a bacterial component as an active ingredient is affected depending on composition of the formulation or process for the preparation thereof. This is also supported by the fact that neither anti-tumor effect and infection-preventing effect nor an immunopotentiating activity are provided by administrating solely a bacterial component in an aqueous solution or suspension, whereas anti-tumor effect and infection-preventing effect are provided by means of administering a bacterial component formulated into an oil-in-water emulsion by dispersing it in an oil with a dispersing device such as a homogenizer and emulsifying the dispersion in a surfactant solution (Cancer Research, 33, 2187-2195 (1973), J. Nat. Cancer Inst., 48, 831-835 (1972), J. Bacteriol., 94, 1736-1745 (1967), Gann, 69, 619-626 (1978), J. Bacteriol., 92, 869-879 (1966)).

We found that, in order to prepare the oil-in-water emulsion as mentioned above in a large scale while retaining its efficient immunopotentiating activity, it is necessary to encapsulate appropriately the bacterial component in an oil, and, to this end, it is suitable that an organic solvent is used as a dispersion-aiding solvent. According to the present invention, any difficulty in the dispersion process caused by use of the oil in a quite small amount relative to water can be eliminated by dispersing a bacterial component having an immunopotentiating activity in a mixture of an oil and a dispersion-aiding solvent comprising an organic solvent. The use of an aiding-solvent comprising an organic solvent in dispersion process enables to control a total amount of the preparations, and the adjustment of amount of the aiding-solvent to be similar to that of the final formulation enables the preparation with only one device for dispersion/emulsion through the whole preparation steps. This makes possible the production of an oil-in-water emulsion in a large scale, and clears the way to the development as pharmaceutics. For information purpose, whether or not a bacterial component is appropriately encapsulated in an oil may be shown by presence or absence of agglutination reaction caused by addition of lectin shows, as discussed hereinafter.

Thus, the second solution of the problem according to the present invention is summarized by;

(1) A process for preparation of an oil-in-water emulsion wherein the emulsion is negative for agglutination reaction with lectin, and a bacterial component is encapsulated in an oil, which comprises the following steps:

(a) stirring a mixture of a bacterial component, an oil, and a dispersion-aiding solvent to disperse the bacterial component in the mixture;

(b) evaporating off the dispersion-aiding solvent to form an oil droplet wherein the bacterial component is encapsulated in the oil; and then, (c) adding an aqueous solution containing a surfactant thereto, and emulsifying the mixture:

(2) The process for preparation of an oil-in-water emulsion according to the above (1), wherein the bacterial component is a BCG-CWS or a CWS of *Nocardia rubra:*

(3) The process for preparation of an oil-in-water emulsion according to the above (1), wherein the bacterial component is a BCG-CWS, and the oil is squalane:

(4) The process for preparation of an oil-in-water emulsion according to the above (1), (2) or (3), wherein the dispersion-aiding solvent is ethanol or toluene: and (5) The process for preparation of an oil-in-water emulsion according to the above (1), (2), (3), or (4), wherein the oil droplet is dispersed in a manner that the diameter of the particle is about 100 μm or less.

According to the second solution of the problem as described above, it became possible to produce in a large scale an oil-in-water emulsion comprising a bacterial component as an active ingredient while retaining an immunopotentiating activity. However, we found that, during the production steps, considerable amounts of a bacterial component are not emulsified adhering to an emulsifying/dispersing device as an insoluble material, which constitutes a quite disadvantage in view of efficient use of a bacterial component.

As a result of studies on emulsification and formulation of a bacterial component, specifically a BCG-CWS, appropriately encapsulated in an oil, we found that an insoluble material that is not formed into a emulsion, and that remains on a wall of an emulsifying/dispersing device after the preparation of the oil-in-water emulsion arises from the property of the oil dispersed with the bacterial component to adhere steady to the walls, and found simultaneously that such adhesion is accelerated by a surfactant. Then, we have successfully diminished the amount of the bacterial component not emulsified and remaining as an insoluble material by means of adjusting the concentration of a surfactant to be used, and besides, performing a two-step emulsification process of rough emulsification and adequate emulsification. Specifically, we found that the two-step emulsification process is very useful, which comprises, as rough emulsification, stirring gently the mixture containing a surfactant at a sufficiently low concentration to prevent acceleration of bacterial component adhesion, and performing emulsification, followed by, optionally, adjusting the concentration of the surfactant in the whole solution by adding a minimum amount of the surfactant necessary to obtain a desired particle diameter distribution, and stirring vigorously the mixture, thereby providing a desired emulsification. It has been shown that the oil-in-water emulsion obtained by the process for preparation of the present invention does not contain the bacterial component remained on and adhesive to the walls as an insoluble material, and namely the most of bacterial component being used is contained in the emulsified formulation. In other words, it has been shown that an amount of the bacterial component in the oil-in-water emulsion is nearly equal to the loaded amount of the component to be emulsified.

Thus, the third solution of the problem according to the present invention is summarized by;

(1) A process for preparation of an oil-in-water emulsion, which comprises the following steps:

(a) stirring a mixture of a bacterial component, an oil, and a dispersion-aiding solvent to disperse the bacterial component in the mixture;

(b) evaporating off the dispersion-aiding solvent; and then;

(c) performing the following two-step emulsification process which comprises adding an aqueous solution containing a surfactant:

i) adding an aqueous solution containing a surfactant at a low concentration to the evaporated material, and stirring gently the mixture, thereby performing rough emulsification; and ii) optionally, adjusting the concentration of the surfactant in the roughly emulsified solution, and stirring vigorously the mixture, thereby performing adequate emulsification in order to provide a desired particle diameter distribution:

(2) The process for preparation of an oil-in-water emulsion according to the above (1), wherein an amount of the surfactant in the aqueous solution containing the surfactant at a low concentration used in rough emulsification of the two-step emulsification process is 10% or less of the oil:

(3) The process for preparation of an oil-in-water emulsion according to the above (1) or (2), wherein the surfactant is Polysorbate 80 (Tween80).

(4) The process for preparation of an oil-in-water emulsion according to the above (1), (2), or (3), wherein the bacterial component is a BCG-CWS or a CWS of *Nocardia rubra.*

(5) The process for preparation of an oil-in-water emulsion according to the above (1), (2), (3), or (4), wherein the bacterial component is a BCG-CWS, and the oil is squalane.

Hereinafter, the present invention is further described.

In the first aspect, the present invention provides a stable formulation useful for immunotherapy for cancers, which is obtainable by lyophilization of an oil-in-water emulsion comprising a bacterial component having an immunopotentiating activity, an oil, a surfactant, a stabilizer and the like.

In the present invention, a bacterial component having an immunopotentiating activity includes a dead bacterium, and a CWS, a muramyl dipeptide (MDP), a lipopolysaccaride (LPS), a mannan, and a glucan, each of which is derived from a bacterium, and a derivative thereof. Dead bacteria are exemplified by a dead *Mycobacterium tuberculosis* typus humanus, and the like. Bacteria from which CWS is derived are exemplified by Mycobacteriaceae, Nocardiaceae, Corynebacteriaceae, and the like. Among them, BCG of *Mycobacterium bovis*, and *Nocardia rubra* are preferred. These CWSs may be obtained in form of an insoluble residue by a purification process which comprises crashing the cells with a physical means, removing nucleic acids and proteins from the cell debris, and then delipidating the resultant material, and the preparation of thereof is well-known (J. Nat. Cancer Inst., 52, 95-101 (1974)). The bacterial component is preferably used in the oil-in-water emulsion in a concentration of 0.1 to 10 mg/ml.

In the present invention, an oil includes a mineral oil, or an animal and vegetable oil such as described in Immunology, 27, 311-329 (1974). The mineral oil is exemplified by a liquid petrolatum, a bayol (Bayol F), Drakeol-6VR, and the like. The vegetable oil is exemplified by a peanut oil, a sesame oil, AD-65 (a mixture of a peanut oil, Arlacel, and aluminum monostearate), and the like. The animal oil is exemplified by squalane, and a terpenoid derivative such as squalene, and the like. Among them, Drakeol-6VR, and squalane are preferred.

The oil is suitably used in the oil-in-water emulsion in a concentration range of 0.01 to 30% w/w, preferably 0.01 to 10% w/w, and more preferably 0.01 to 5.0% w/w.

In the present invention, a surfactant is not limited to a particular species as long as it is used in a pharmaceutical formulation. It includes a phospholipid, a nonionic surfactant, and the like. The phospholipid is exemplified by phosphatidyl amine, phosphatidyl thanol amine, phosphatidyl inositol, phosphatidyl serine, sphingomyelin, lecithin, and the like. A hydrogenated phospholipid may be used. The nonionic surfactant is exemplified by polyethylene glycol, poly(oxyethylene)-polyoxypropylene copolymer, Polyoxyethylene Hydrogenated castor oil, a poly(oxyethylene) castor oil derivative, a poly(oxyethylene) sorbitan fatty acid ester such as poly(oxyethylene) sorbitan monolaurate (Polysorbate 20), poly(oxyethylene) sorbitan monopalmitate (Polysorbate 40), poly(oxyethylene) sorbitan monostearate (Polysorbate 60), and poly(oxyethylene) sorbitan monooleate (Polysorbate 80), and a sorbitan fatty acid ester such as sorbitan monolaurate (Span 20), sorbitan monopalmitate (Span 40), sorbitan monostearate (Span 60), and sorbitan monooleate (Span 80). Preferred surfactant includes egg yolk phosphatidyl amine, egg yolk lecithin, soybean lecithin, and Polysorbate 80, and more preferred surfactant includes Polysorbate 80.

The surfactant is suitably used in the oil-in-water emulsion in a concentration range of 0.01 to 10% w/w, and preferably, 0.01 to 5.0% w/w. Each surfactant may be used solely, or in combination with other several ones, if necessary.

In the present invention, a stabilizer includes a polysaccharide, an amino acid, a protein, urea, and sodium chloride. The polysaccharide is exemplified as a preferred one by dextran, starch, maltodextrin, cellulose, polyvinylpyrrolidone, sodium alginate, and the like. The amino acid is preferably a neutral amino acid such as alanine, glycine, proline, and more preferably, glycine among the neutral amino acids. The protein is exemplified as a preferred one by albumin, a gelatin, a collagen, and the like. Each stabilizer may be used solely, or in combination with other several ones, if necessary.

The stabilizer is suitably used in the oil-in-water emulsion in a concentration range of 0.1 to 20% w/w, and preferably, 0.1 to 10% w/w.

A dispersion solvent to be used to re-disperse a lyophilized formulation of the present invention includes injectable water (injectable distilled water), a physiological saline and the like, which are a medium for dispersing emulsion particles, but is limited to a particular species as long as it can be injected as a dispersion solvent.

In the present invention, an excipient may be added in order to form a lyophilized preparation into a lyophilized cake, if desired. Most excipients also function as an agent for rendering isotonic. The excipient is exemplified as a preferred one by a saccharide, an amino acid, urea, sodium chloride, and the like. The saccharide is exemplified by a monosaccharide, a disaccharide, and a sugar alcohol. The monosaccharide includes glucose, fructose, and the like, the disaccharide includes maltose, lactose, trehalose, sucrose, and the like, and the sugar alcohol includes mannitol, sorbitol, and the like.

The amino acid includes alanine, glycine, and the like. Each excipient may be used solely, or in combination with other several ones, if necessary.

The excipient is suitably used in the oil-in-water emulsion in a concentration range of 0.1 to 30% w/w, and preferably, 1 to 20% w/w.

In addition, an antioxidant, an antiseptic, an agent for rendering isotonic, a buffering agent, etc., each of which may be used in pharmaceutical formulations may be added at any stage as required, if necessary. It is often that a concentration of 10% w/w or less in an oil-in-water emulsion is sufficient.

Preferable lyophilized formulation of the present invention shows, in an oil-in-water emulsion both before lyophilization and after re-dispersion, a single peak of particle diameter distribution, and does not an large change in turbidity (relative absorbance), and more preferable formulation shows a change in turbidity by 50% or less relative to that before lyophilization. The average particle diameter is in range of 0.1 to 20 μm, preferably 1 to 10 μm, and more preferably 1 to 5 μm.

The phrase "showing (or with) a single peak of particle diameter distribution" herein means a condition that the emulsion shows a sufficient emulsification and a particular oil droplet therein is physically stable, and, for example, a condition that the emulsion shows a similar particle diameter distribution both before and after lyophilization, without the average particle diameter after lyophilization deviating largely from that before lyophilization. Conversely, a particle diameter distribution with two or more peaks means a condition that the emulsion is in a progressive condition of aggregation or union, and means that it is not a stable emulsion.

Average particle diameter, particle distribution, and turbidity may be determined using a laser diffraction particle size analyzer (SALD3000, SHIMADZU Corp., hereinafter it is used likewise), for example.

The present invention also provides a process for preparation of the lyophilized formulation as described above. According to the process, an oil-in-water emulsion comprising a bacterial component, an oil, a surfactant, an excipient, a stabilizer, etc. is first prepared before lyophilization. Such an oil-in-water emulsion is prepared by, for example, adding a bacterial component at a concentration as described above to an oil at a concentration as described above, adding further an aqueous solution of a surfactant, an excipient, a stabilizer and another additive to the mixture, and then emulsifying the resultant mixture until forming an oil-in-water emulsion with an average particle diameter as described above with a dispersing or emulsifying device such as a Potter-Elvehjem type homogenizer, a homomixer, an ultrasonic homogenizer, MICROFLUIDIZER™, NANOMIZER™, ULTIMIZER™, Gaulin homogenizer type high pressure homogenizer, and the like. If necessary from viewpoint of preparation, an additive such as an excipient, or a stabilizer may be added to the oil-in-water emulsion that have been prepared as shown above.

Second, the resultant oil-in-water emulsion is lyophilized, usually replaced with $N_2$ in a vial, and finally the vial is sealed to obtain a lyophilized formulation.

The lyophilized formulation can be quickly re-dispersed in a suitable dispersion solvent such as water, thus providing reconstitution of an oil-in-water emulsion showing an average particle diameter, particle diameter distribution, or turbidity similar to those before lyophilization. Amount of the dispersion solvent is not limited to a particular amount, and may be in a range of 0.5 to 2 times than that before lyophilization, but depending on its use.

In the second aspect, the present invention provides a process for preparation of an oil-in-water emulsion, which comprises using a mixture of a bacterial component, an oil, and a dispersion-aiding solvent comprising an organic solvent.

According to the process, a mixture of bacterial component having an immunopotentiating activity, an oil, and a dispersion-aiding solvent is first treated with a dispersing or emulsifying device, and then, the dispersion-aiding solvent is evaporated off. To the residue caused by the evaporation, an isotonic solution containing a surfactant, a stabilizer, etc. is added, and the mixture is treated with a dispersing or emulsifying device to obtain an oil-in-water emulsion, which retains a desired immunopotentiating activity.

A bacterial component used in the present invention, particularly a BCG-CWS or a CWS of *Nocardia rubra* is insoluble in water or an organic solvent, and even in an oil. It was very difficult to disperse homogeneously and constantly a bacterial component in an oil via a direct means especially because an oil should be used in a very small amount, and should have a very viscous property. However, when using an organic solvent that is removable afterward as a dispersion-aiding solvent, it has made it possible to obtain readily and constantly a homogeneous dispersion compared to the direct use of an oil in dispersion. An organic solvent can be used in a large amount since it can be removed afterward, and an organic solvent shows a low viscosity, and therefore can be used to constantly prepare readily a homogeneous dispersion with a dispersing device. Then, the organic solvent is removed in situ to obtain an oily material wherein a bacterial component is hom generously dispersed.

As described above, use of a dispersion-aiding solvent comprising an organic solvent has made it possible to obtain constantly a bacterial component as described above that is appropriately dispersed and is sufficiently encapsulated into an oil. For example, a conventional process, which does not comprise use of a dispersion-aiding solvent, was difficult to prepare a homogeneous, good dispersion in a Potter type homogenizer every time since the oil is used in a small amount, whereas use of a dispersion-aiding solvent has provided constant preparation of a good dispersion. Thus, the process for preparation according to the present invention accomplished the purpose for preparation of a good dispersion wherein a bacterial component is appropriately encapsulated in an oil by an industrial means.

By selecting a suitable dispersion-aiding solvent, further, there has been able to obtain a preparation wherein a particle of a bacterial component as described above having a fine particle diameter is appropriately dispersed after evaporating off the dispersion-aiding solvent may be obtained, and a preparation wherein the crude particles are not visible. The crude particles that are visible have usually a diameter of about 100 μm or more.

In order to determine if a bacterial component is appropriately encapsulated in an oil to an extent as desired, agglutination reaction with lectin or the like can be used, which reaction is further described hereinafter.

A dispersion-aiding solvent useful in the present invention includes an organic solvent that can be evaporated off by an easy procedure, for example, under heating, or in vacuo in a nitrogen stream. Preferred organic solvents include a solvent of Class 2 or 3 described in the ICH Guideline for Residual Solvents (Q3C). More preferred solvents include an aromatic hydrocarbon such as toluene, a aliphatic hydrocarbon such as cyclohexane, a halogenated hydrocarbon such as dichloromethane, chloroform, trichloroethylene, a lower alcohol such as ethanol, isopropanol, an acetate such as ethyl acetate, an ether such as ethyl ether, and a ketone solvent such as acetone. Still more preferred solvents include a lower alcohol such as ethanol, isopropanol, a halogenated hydrocarbon such as chloroform, an aromatic hydrocarbon such as toluene. Most preferred solvents include ethanol, chloroform, and toluene.

A temperature for evaporating off a solvent may be optionally selected depending on the boiling point or vapor pressure of the solvent. Since a high temperature causes inactivation of a bacterial component, the temperature is desirably 100° C. or less not causing its inactivation. Preferably, the temperature is 80° C. or less, and more preferably, 70° C. or less.

An aqueous solution useful in this process for preparation is a dispersion medium for emulsion particles as mentioned above. The solution includes an isotonic solution such as a physiological saline, and injectable water (injectable distilled water), but is limited to a particular species as long as it is an injectable dispersion solvent. An agent for rendering isotonic includes a saccharide, an amino acid, urea, sodium chloride, and the like. The saccharide is exemplified by a monosaccharide, a disaccharide, and a sugar alcohol. The monosaccharide includes glucose, fructose, and the like, the disaccharide includes maltose, lactose, trehalose, sucrose, and the like, and the sugar alcohol includes mannitol, sorbitol, and the like. The amino acid includes alanine, glycine, and the like. Each agent may be used solely, or in combination with other several ones, if necessary. The agent is suitably used in the oil-in-water emulsion in a concentration range of 0.1 to 30% w/w, and preferably, 1 to 20% w/w.

Additionally, an antioxidant, an antiseptic, a buffering agent, etc., each of which may be used in pharmaceutical formulations may be added, if necessary. It is often that a concentration of 10% w/w or less in an oil-in-water emulsion is sufficient.

In the third aspect, the present invention provides a process for preparation of an oil-in-water emulsion, which comprises mixing a bacterial component, an oil, and a dispersion-aiding solvent to disperse the bacterial component in the mixture; evaporating off the dispersion-aiding solvent; and then, performing the two-step emulsification process. Specifically, the present invention comprises, after evaporating off the dispersion-aiding solvent, adding an aqueous solution containing a surfactant at a low concentration to the bacterial component appropriately encapsulated in the oil, and stirring gently the mixture with a dispersing/emulsifying device, thereby performing rough emulsification; and, then, adjusting the concentration of the surfactant in the solution by adding an additional surfactant thereto, and stirring vigorously the mixture with a dispersing/emulsifying device, thereby obtaining a desired oil-in-water emulsion.

The two-step emulsification process enables an oil-in-water emulsion to take up an almost quantitative amount of the bacterial component being used.

In the first rough emulsification of the two-step emulsification process, a surfactant to be used in this step is desirably at a concentration of about 10% or less relative to an oil since the bacterial component tends to increase in adhesion to a device, etc. when a surfactant is at a concentration of about 10% or more relative to an oil. The surfactant is preferably used in a concentration of 0.2 to 8% of an oil, and more preferably 1 to 8% of an oil. Thus, an aqueous solution containing a surfactant at a low concentration, which is used in the rough emulsification, is an aqueous solution containing a surfactant in an amount of about 10% or less of an oil to be used. It should be noted that a concentration of the surfactant used in the rough emulsification does not exceed that of a surfactant used in adequate emulsification.

Then, a surfactant used in the adequate emulsification is necessary to be in the minimum amount necessary to obtain a desired particle size distribution. In some cases, the concentration of the surfactant may be the same as that during the rough emulsification, or in other cases, the surfactant concentration in the whole solution may be adjusted to be higher than the surfactant concentration used in the rough emulsification. A concentration of the surfactant in a surfactant solution used to adjust the surfactant concentration in the whole solution is not limited as long as the surfactant solution can be used in a small amount to adjust the concentration, and, for example, Polysorbate 80 can be used in a concentration of about 5 to about 15% in an aqueous solution. In the emulsification step, the surfactant is necessary to be in a concentration of about 10% or more of an oil, and is adjusted to be preferably in a concentration of about 10 to about 20% of an oil, more preferably in a concentration of about 15 to about 20% of an oil. The adjustment of the surfactant concentration during the adequate emulsification is to adjust a surfactant concentration in order to prepare an emulsion having a desired particle size distribution.

After performing the adequate emulsification, if desired, an additional amount of the surfactant may be added to prepare a solution having a higher amount of the surfactant, and then, the solution may be also stirred with an emulsifying device to provide a solution having a sharp distribution of particle size. If necessary, a stabilizer or an agent for rendering isotonic may be added to these aqueous solutions. Each surfactant may be used solely, or in combination with other several ones, if necessary.

As to a stirring condition for emulsification, a gently stirring condition includes emulsification at 5000 to 7000 rpm turning speed in case of IKA ULTRA-TURRAX® T-25 (shaftdrive S25KV-25F), and a vigorously stirring condition includes emulsification at 10000 to 25000 rpm turning speed. As to temperature for emulsification, a high temperature is desirable, but about 40 to 80° C. is suitable in view of evaporation of the aqueous portion. When a surfactant to be used is bound to poly(oxyethylene), the temperature is desirably adjusted viewing its cloud point.

The period of time for emulsification may be optionally determined so that a desired particle size distribution of an emulsion to be prepared is attained while measuring the particle size distribution with an apparatus for particle size distribution measurement.

The oil-in-water emulsion obtained by dispersing in a solvent the lyophilized formulation as described in the first aspect of the present invention, and the oil-in-water emulsion prepared by the process as described in the second and third embodiment must have an immunopotentiating activity. To do so, a bacterial component is necessary to be appropriately encapsulated in an oil as described above, and whether or not the encapsulation is sufficient may be examined by assay of the agglutination reaction with lectin.

The assay involves an interaction between lectin and a sugar chain of the bacterial component (arabinogalactan). Sufficient encapsulation of the bacterial component means sufficient encapsulation of the sugar chain, and therefore, the interaction does not arise when the sugar chain is appropriately encapsulated. In other words, when the agglutination reaction is negative, the major component is appropriately encapsulated. Because the emulsion is characterized in that anti-tumor effect and infection-preventing effect via an immunopotentiating activity are provided by the sufficient encapsulation of a bacterial component in an oil, negative index of the lectin agglutination can be used to demonstrate either presence or absence of the biological activity.

The agglutination reaction herein refers to a reaction wherein an agglutination of a bacterial component can be visually recognized by a fluorescent microscopy or a phase-contrast microscope. For example, when lectin is added to the BCG-CWS oil-in-water emulsion to be expected to show the agglutination reaction, agglutination in the emulsion may be visually recognized as shown in FIG. 15. Consequently, "positive" for the agglutination reaction means that the agglutination mass is developed. Contrary, "negative" means that the agglutination mass is not developed, and that the bacterial component encapsulated in the oil is dispersed almost uniformly.

Recognition test for the agglutination reaction comprises mixing the emulsion formulation of the present invention and a solution of lectin (concanavalin A) by pipetting, allowing the mixture to stand at 25° C. for 30 minutes or more, and recognizing the presence or absence of the agglutination reaction with a phase-contrast microscope or the like. Examples of the results include the cases of the formulation of only bacterial component without any oil (oil free; Reference Example 2.3), or the formulation of the improved process of the well-known preparation (Reference Example 2.2), both which show the presence of the agglutination reaction as shown in FIGS. 10, and 15. On the other hand, the emulsion formulation wherein a bacterial component is appropriately encapsulated in an oil demonstrates the absence of the agglutination reaction as shown in FIGS. 12 to 14 (Examples 2.2, 3.1, 3.2). As shown above, the observation of the presence or absence of the agglutination reaction enables to recognize a range of the encapsulation in the oil.

The oil-in-water emulsion prepared by the process of the present invention as well as the lyophilized formulation of the first aspect of the invention, which has been re-dispersed in a dispersion solvent can be administered parenterally, for example, by injection. Dosage form to be administered may be varied depending on a therapeutic purpose, and is not limited to a particular form. Dosage form that is usually used includes an injection form for hypodermical or intradermal administration.

Although the amount and the number of the invention to be administered may be varied depending on the disease to be treated, the symptom, the age and the body weight of a particular patient, it is possible to usually administer 0.1 to 200 μg, and preferably 1 to 100 μg per administration every week or every four weeks to an adult in case of a parenteral administration, particularly injection.

BRIEF DESCRIPTION OF THE DRAWING

The following descriptions are concerned in Figures.

FIG. 11 shows the result of lectin agglutination reaction test regarding the formulation of Example 2.1 obtained by the ethanol solvent-dispersion improvement.

FIG. 12 shows the result of lectin agglutination reaction test regarding the formulation of Example 2.2.

FIG. 13 shows the result of agglutination reaction evaluation regarding the formulation of Example 3.1.

FIG. 14 shows the result of agglutination reaction evaluation regarding the formulation of Example 3.2.

BEST MODE FOR CARRYING OUT THE INVENTION

Examples

Figure 1:
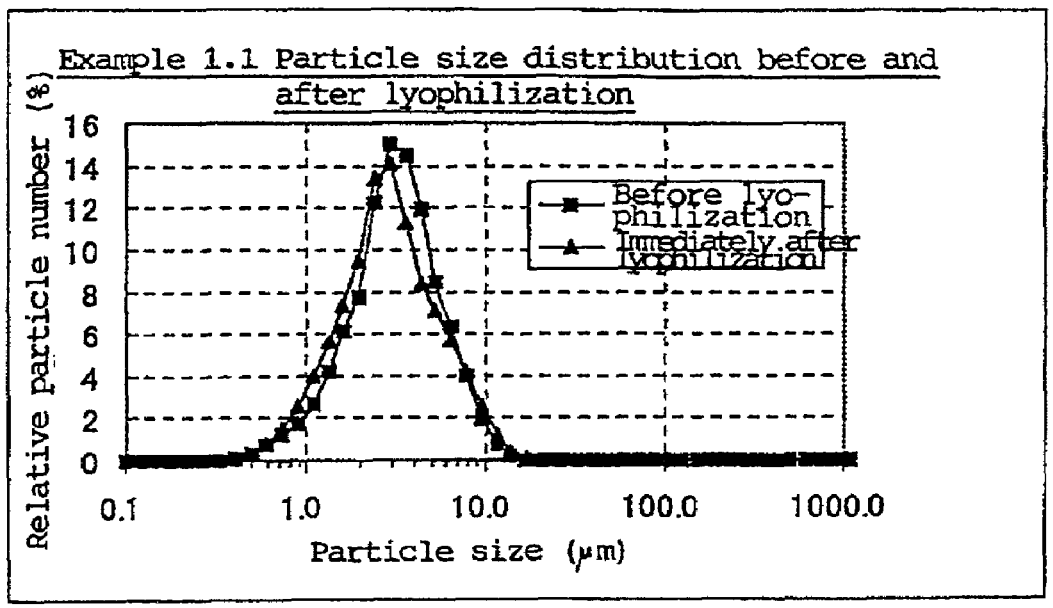
FIG. 1 shows the average particle size and the particle size distribution regarding each of the oil-in-water emulsion obtained in Example 1.1 that is before lyophilization, and the preparation obtained by re-dispersing the lyophile of the emulsion immediately after lyophilization.

The present invention of the three aspects is further illustrated by the examples, the references, and the test examples as described below, but is not restricted by them in any respect.

Example 1.1

To the dispersion of 4 mg of a CWS derived from the BCG strain of *Mycobacterium* genus as a bacterial component, and 20 μL of squalane (0.5% w/w) as an oils which dispersion had been prepared with a Potter-Elvehjem type homogenizer, 4 mL of an aqueous solution of 0.2% w/w Polysorbate 80/300 mM (2.3% w/w) glycine was added, and the mixture was emulsified to obtain an oil-in-water emulsion having an immunopotentiating activity.

Each of 0.5 mL aliquots of the oil-in-water emulsion was portioned into 4 mL vials respectively, and lyophilized to obtain lyophilized formulations of the present invention. Lyophilization was performed using a Kyowa type lyophilizer (G-1, RL-100BS, Kyowa Vacuum Engineering, Ltd.).

Example 1.2

According to the same procedure as that of Example 1.1 except that urea was used as a stabilizer instead of glycine, an oil-in-water emulsion and the lyophilized formulation thereof were obtained.

Example 1.3

One gram of a BCG-CWS as a bacterial component was added to a mixture of 32 g of squalane and 300 ml of toluene, and the resultant mixture was shaken or treated with ultrasonic at a room temperature to perform dispersion. Then, the dispersion was heated at 60° C. under a flow of nitrogen to evaporate the toluene. After that, rough emulsification with a homomixer was performed on the residue that had been added with 1.8 L of an aqueous solution of 0.02% w/w Polysorbate 80/4.5% glycine, and further, after addition of 200 mL of 10% w/w Polysorbate 80, adequate emulsification was performed, thereby obtaining an oil-in-water emulsion.

Each of 0.5 mL aliquots of the oil-in-water emulsion was portioned into vials respectively, and lyophilized to obtain lyophilized formulations of the present invention. Lyophilization was performed using a Kyowa type lyophilizer (G-1, RL-100BS, Kyowa Vacuum Engineering, Ltd.).

Reference 1.1

According to a similar procedure to that of Example 1.1 except that a sugar alcohol described in the prior art (Japanese Patent Publication (kokoku) No. 1291/1988), mannitol, was used as a stabilizer instead of glycine, an oil-in-water emulsion and the lyophilized formulation thereof were obtained.

Constitutional components and the amounts thereof used in Examples 1.1 and 1.2, and Reference 1.1 are described in Table 1.

TABLE 1

|  | Example 1.1 | Example 1.2 | Reference 1.1 |
| --- | --- | --- | --- |
| Bacterial component | 4 mg of CWS derived from strain of Mycobacterium genus (BCG-CWS) | 4 mg of CWS derived from BCG strain of Mycobacterium genus (BCG-CWS) | 4 mg of CWS derived from BCG strain of Mycobacterium genus (BCG-CWS) |
| oil | 20 μL (0.5% w/w) of squalane | 20 μL (0.5% w/w) of squalane | 20 μL (0.5% w/w) of squalane |
| Surfactant, and stabilizer | 4 mL of an aqueous solution of 0.2% w/w Polysorbate 80/300 mM (2.3% w/w) glycine | 4 mL of an aqueous solution of 0.2% w/w Polysorbate 80/ 300 mM (2.3% w/w) urea | 4 mL of an aqueous solution of 0.2% w/w Polysorbate 80/300 mM (2.3% w/w) mannitol |

A laser diffraction particle size analyzer (SALD3000, SHIMADZU Corp., hereinafter it is used likewise) was used to determine absorbance, average particle diameter, and particle size distribution of each of the oil-in-water emulsions prepared in Examples 1.1 and 1.2, and Reference 1.1, which was before lyophilization, as well as oil-in-water emulsions prepared by re-dispersing the lyophilized formulations of these examples immediately after lyophilization. The oil-in-water emulsions that were re-dispersed immediately after lyophilization were prepared by dispersing each lyophile in 0.5 mL of injectable distilled water.

TABLE 2

|  | Average particle diameter | | Change of particle size distribution* | Absorbance (relative value) Immediately after lyophil. Before lyophil. |
| --- | --- | --- | --- | --- |
|  | Before lyophil. | Immediately after lyophil. | | |
| Example 1.1 | 2.7 μm | 2.6 μm | A | 0.95 |
| Example 1.2 | 2.1 μm | 2.5 μm | A | 0.90 |
| Reference 1.1 | 2.6 μm | 2.8 μm | B | 0.15 |

*Estimation of change of particle size distribution. "A" shows that the change is small, and "B" shows that the change is significant.

Figure 2:
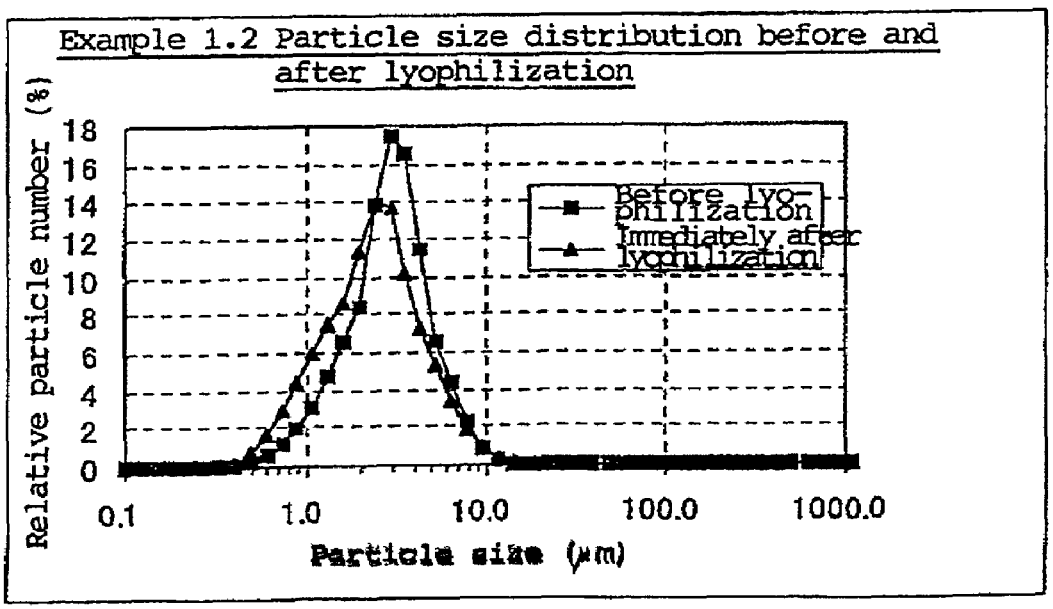
FIG. 2 shows the average particle size and the particle size distribution regarding each of the oil-in-water emulsion obtained in Example 1.2 that is before lyophilization, and the preparation obtained by re-dispersing the lyophile of the emulsion immediately after lyophilization.

In Example 1.1 wherein glycine was used as a stabilizer, and Example 1.2 wherein urea is used, there was little change in the average particle diameter, and the particle size distribution comparing between before and after lyophilization, as shown in FIGS. 1 and 2, and it was possible to reproduce an oil-in-water emulsion similar to the emulsion before lyophilization. Further, the absorbance was not found to change, and the turbidity hardly changed.

Figure 3:
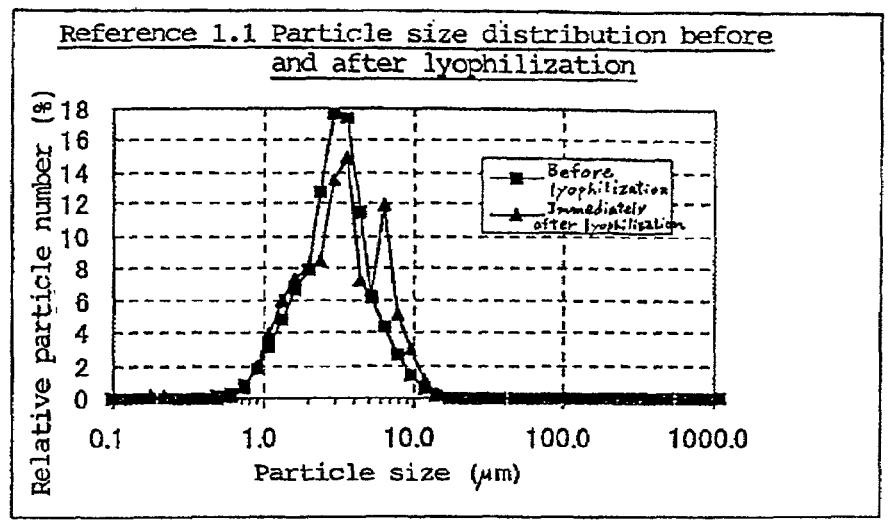
FIG. 3 shows the average particle size and the particle size distribution regarding each of the oil-in-water emulsion obtained in Reference 1.1 that is before lyophilization, and the preparation obtained by re-dispersing the lyophile of the emulsion immediately after lyophilization.

In Reference 1.1 wherein a sugar alcohol described in the prior art (Japanese Patent Publication (kokoku) No. 1291/1988), mannitol, was used as a stabilizer, on the other hand, the particle size distribution having a single peak broke down as shown in FIG. 3, and any difference in absorbance was also found.

Test Example 1.1

Biological Activity Test

The oil-in-water emulsions obtained by re-dispersing the formulations of Examples and Reference in water were compared by a mouse tumor metastasis model system in terms of their biological activity, demonstrating that the lyophilization treatment causes no decrease in biological activity.

Colon26-M3.1 tumor cells were administered into the tail vein of twenty BALB/C mice aged eight weeks at $2.5 \times 10^4$ cells/animal, and the animals were divided into four groups, each consisting of five animals. Twenty four hours later, the animals of the first group received none, and was used as a control. The animals of the second group received via the tail veins a sample prepared by diluting 100 μL of an oil-in-water emulsion similar to the emulsion of Example 1.1 except that the BCG-CWS was not comprised with the same volume of an aqueous solution of 0.2% Polysorbate 80/300 mM glycine. The animals of the third group received via the tail veins a sample prepared by diluting 100 μL of the oil-in-water emulsion of Example 1.1, which was before lyophilzation, with the same volume of an aqueous solution of 0.2% Polysorbate 80/300 mM glycine. The animals of the forth group received via the tail veins a sample prepared by diluting 100 μL of the oil-in-water emulsion obtained by re-dispersing the lyophilized formulation of Example 1.1 with 0.5 mL of distilled water, with the same volume of an aqueous solution of 0.2% Polysorbate 80/300 mM glycine. Two weeks later, thoracotomy was performed on the animals to remove their lungs, and the metastatic focus in the lungs was counted, thus comparing with the counts between the groups. The result is as shown in Table 3.

TABLE 3

| | Inhibition % of metastasis (of the control group 1) |
|---|---|
| 1st group (control) | — |
| 2nd group (without BCG-CWS) | 0 |
| 3rd group (Example 1.1: emulsion before lyophilization) | 52* |
| 4th group (Example 1.1: lyophilized formulation) | 51* |

*p < 0.01, t-test was applied comparing with the 1st group.

Table 3 shows that the lyophilized formulations of the present invention were found no decrease in their biological activity, demonstrating the advantage of the invention.

Test Example 1.2

Stability Test 1

Comparative Experiment

Figure 4:
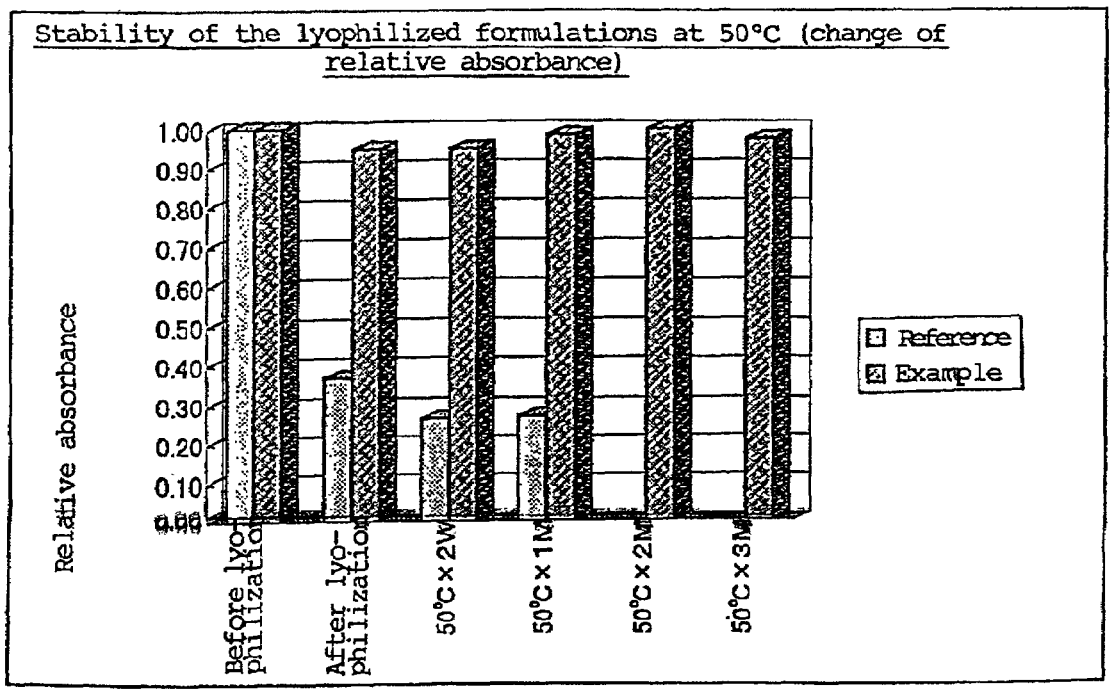
FIG. 4 shows the change of turbidity (relative absorbance) of the emulsion obtained by re-dispersing the formulation that has been preserved at 50° C. with the time course (Test Example 1.2).
Figure 5:
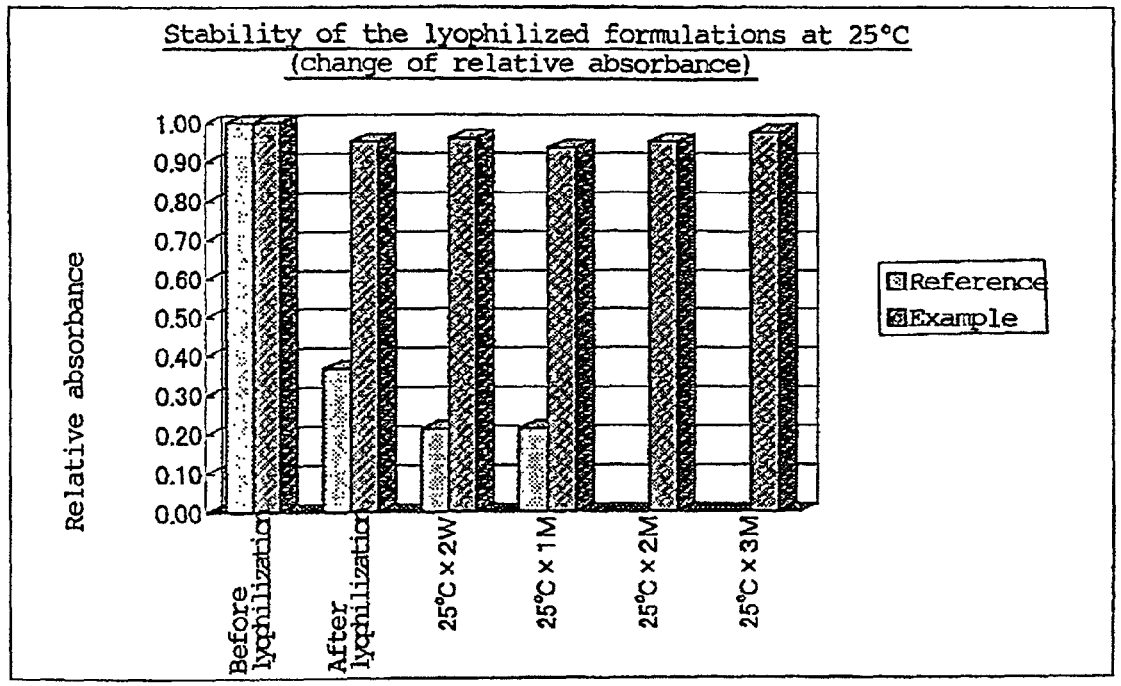
FIG. 5 shows the change of turbidity (relative absorbance) of the emulsion obtained by re-dispersing the formulation that has been preserved at 25° C. with the time course (Test Example 1.2).

After preserved at 50° C. and 25° C. for two weeks, one month, two months, and three months, the lyophilized formulation of the invention obtained in Example 1.1, and the lyophilized formulation obtained in Reference 1.1 were re-dispersed to prepare oil-in-water emulsions, and relative absorbance of each of them was determined thereby examining turbidity change with time course. As described in Tables 4 and 5, and FIGS. 4 and 5, the lyophilized formulations, even after preserved for the long periods of time, show a similar absorbance value to that before lyophilization at any temperature, showing that they have a remarkable stability.

TABLE 4

| | Results of long period preservation at 50° C. x(relative absorbance) | | | | | |
|---|---|---|---|---|---|---|
| | Before lyophilization | After lyophilization | 50° C. × 2 W | 50° C. × 1 M | 50° C. × 2 M | 50° C. × 3 M |
| Example 1.1 | 1.00 | 0.95 | 0.95 | 0.98 | 1.02 | 0.98 |
| Reference 1.1 | 1.00 | 0.37 | 0.26 | 0.27 | —** | —** |

TABLE 5

| | Results of long period preservation at 25° C. x(relative absorbance) | | | | | |
|---|---|---|---|---|---|---|
| | Before lyophilization | After lyophilization | 25° C. × 2 W | 25° C. × 1 M | 25° C. × 2 M | 25° C. × 3 M |
| Example 1.1 | 1.00 | 0.95 | 0.96 | 0.93 | 0.95 | 0.98 |
| Reference 1.1 | 1.00 | 0.37 | 0.21 | 0.21 | —** | —** |

**under the detection limit, so determination being impossible

Test Example 1.3

Stability Test 2

Experiment for Examining the Change of Particle Diameter Distribution

Figure 6:
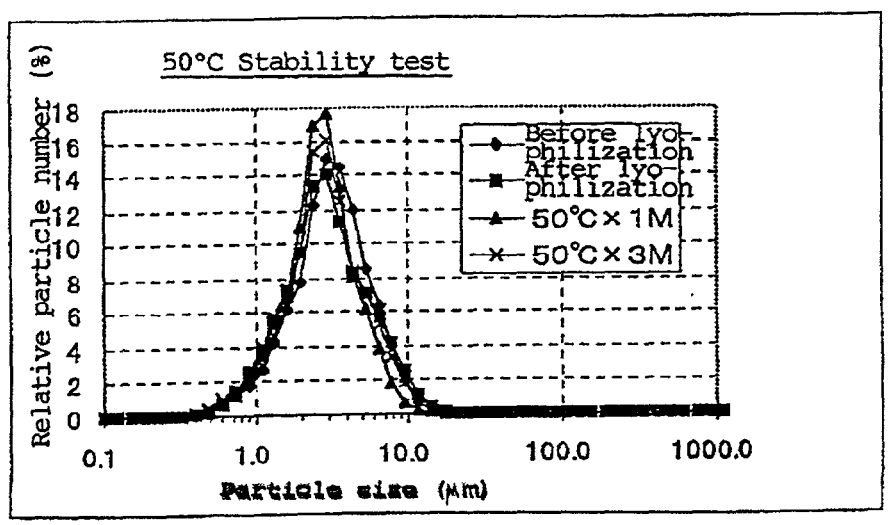
FIG. 6 shows the change of average particle size and particle size distribution of the emulsion obtained by re-dispersing the formulation that has been preserved at 50° C. with the time course (Test Example 1.3).
Figure 7:
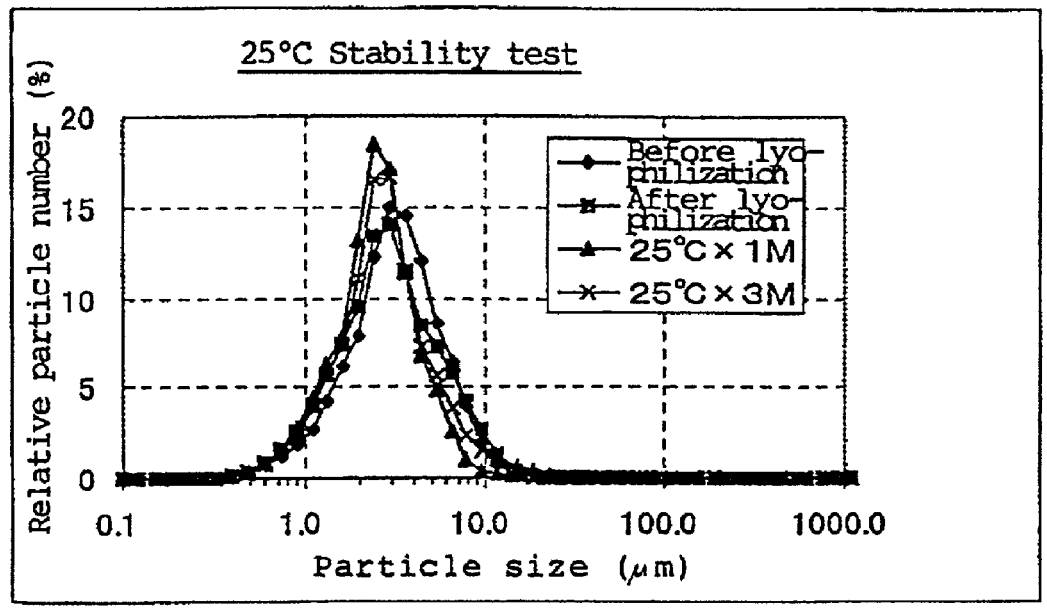
FIG. 7 shows the change of average particle size and particle size distribution of the emulsion obtained by re-dispersing the formulation that has been preserved at 25° C. with the time course (Test Example 1.3).
Figure 8:
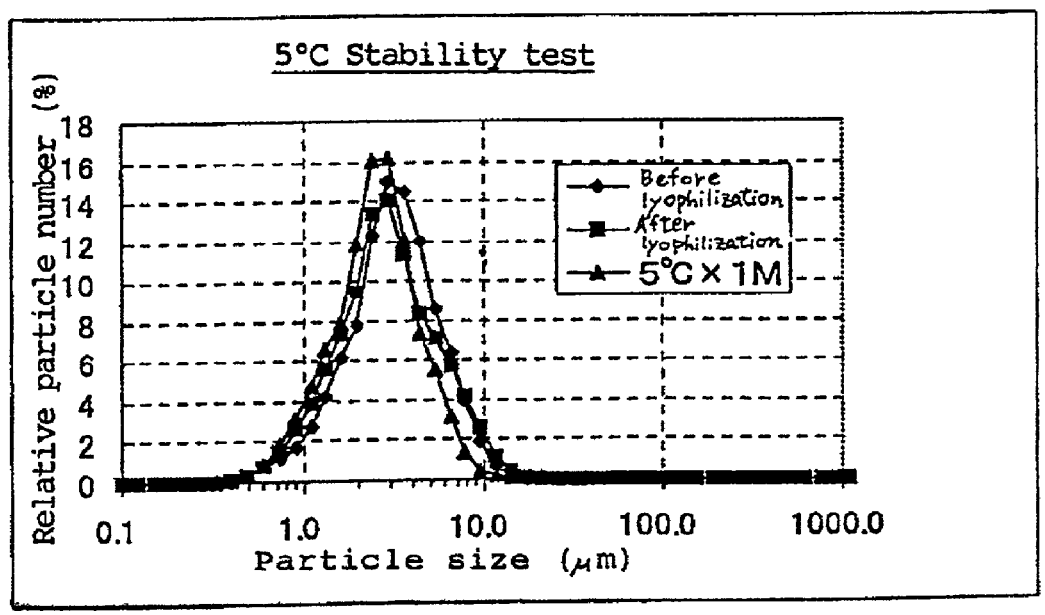
FIG. 8 shows the change of average particle size and particle size distribution of the emulsion obtained by re-dispersing the formulation that has been preserved at 5° C. with the time course (Test Example 1.3).

After preserved at 5, 25, and 50° C. for one month or three months, the lyophilized formulation of the present invention obtained in Example 1.1 was re-dispersed, and changes of average particle diameter and particle diameter distribution were examined with the time course. The result is as shown in Table 6, and FIGS. 6, 7, and 8.

TABLE 6

| | Average particle diameter (μm) | | | |
|---|---|---|---|---|
| Preservation temperature | Before lyophilization | Immediately after lyophilization | 1 M | 3 M |
| 5° C. | 2.7 | 2.6 | 2.2 | 2.3 |
| 25° C. | 2.7 | 2.6 | 2.2 | 2.4 |
| 50° C. | 2.7 | 2.6 | 2.4 | 2.6 |

The lyophilized formulation demonstrated a remarkable stability without any significant changes of the average particle diameter and particle diameter distribution at all temperatures of 5, 25, and 50° C.

Test Example 1.4

Stability Test 3

Experiment for Examining the Change of Particle Diameter Distribution

Figure 9:
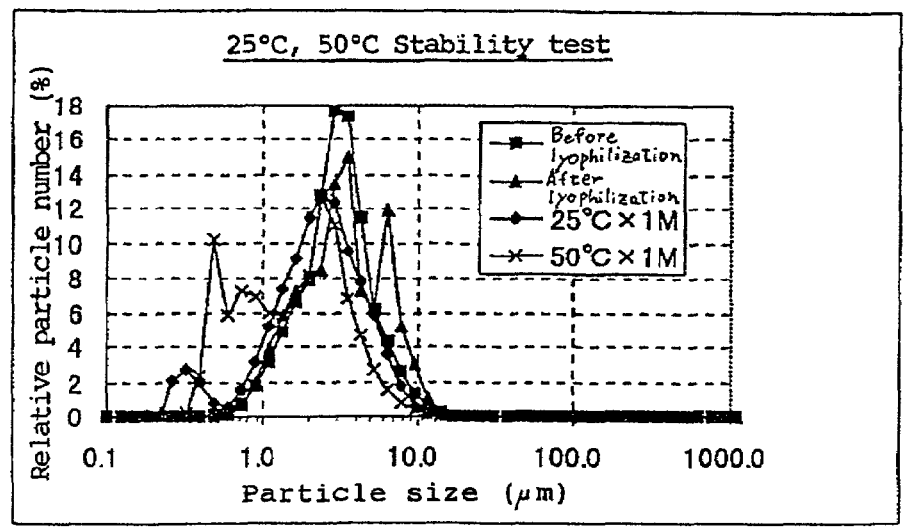
FIG. 9 shows the change of average particle size and particle size distribution of the formulation of Reference 1.1.
Figure 10:
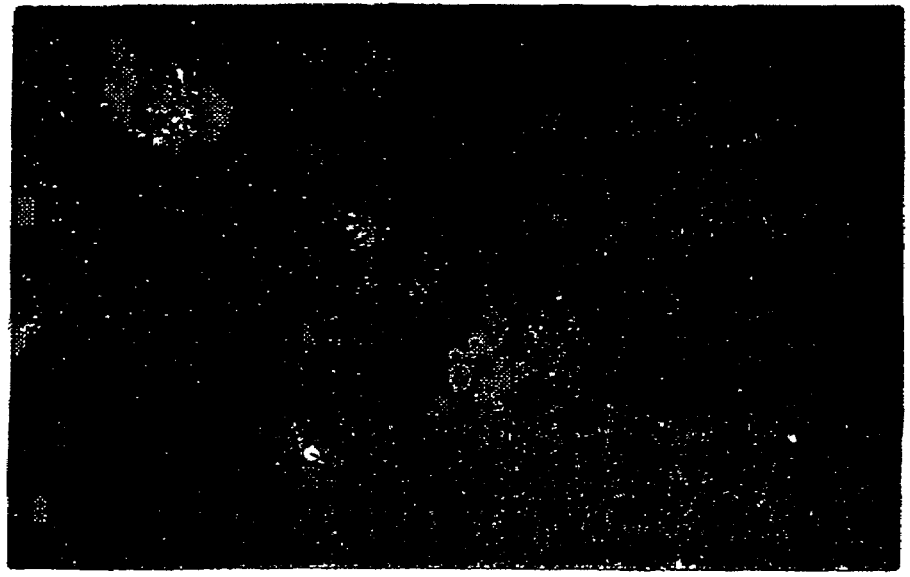
FIG. 10 shows the result of lectin agglutination reaction test regarding the formulation of Reference 2.3, which does not contain an oil.
Figure 1:
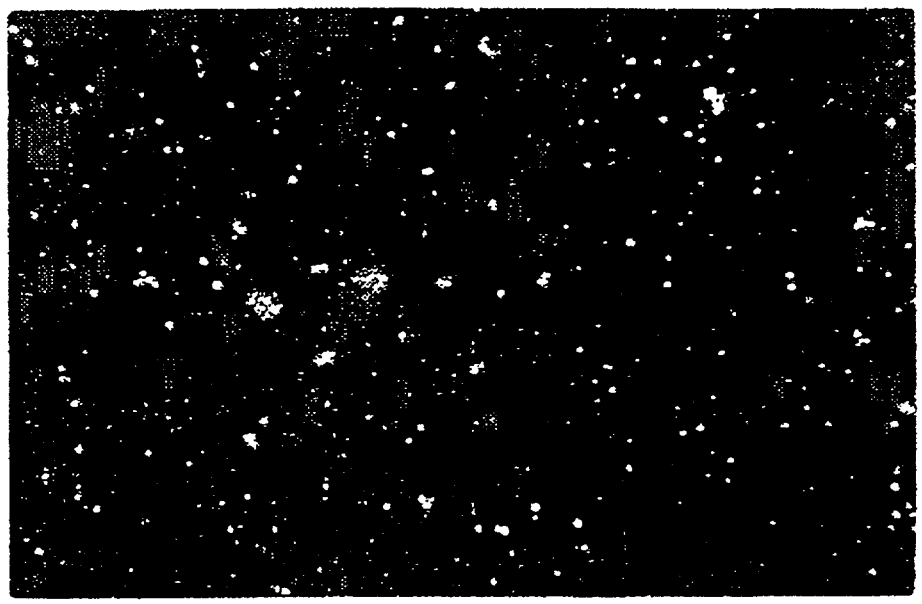
Figure 1:
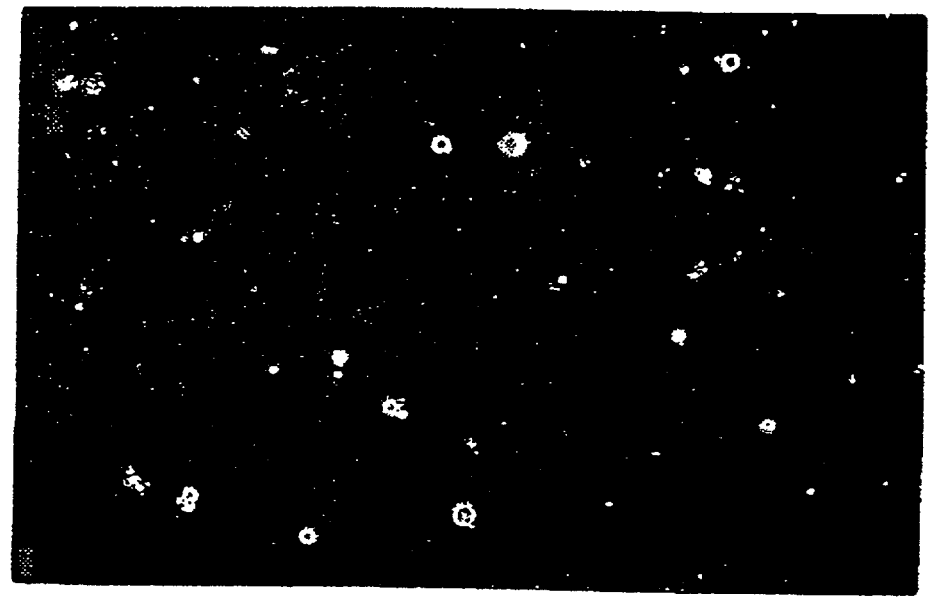
Figure 1:
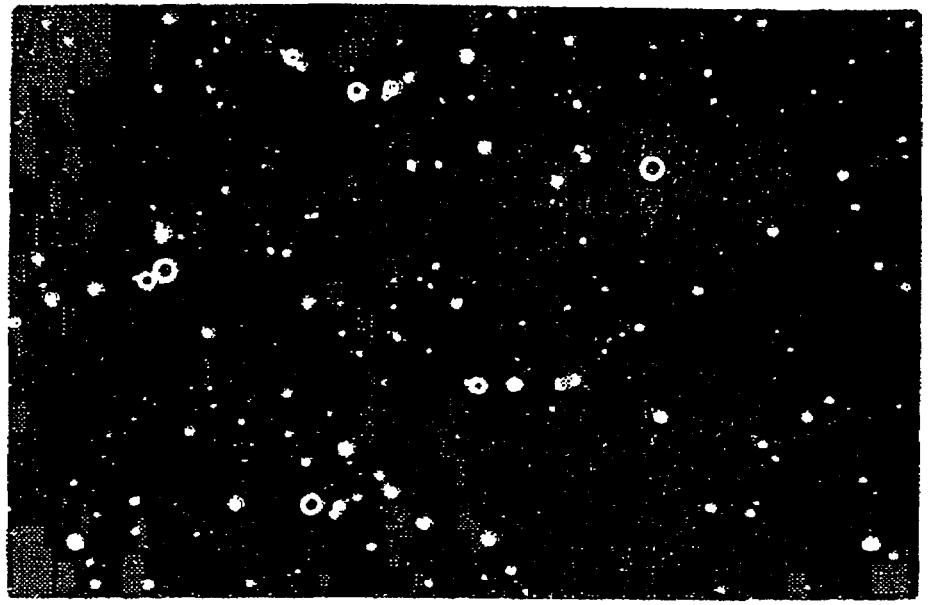
Figure 1:
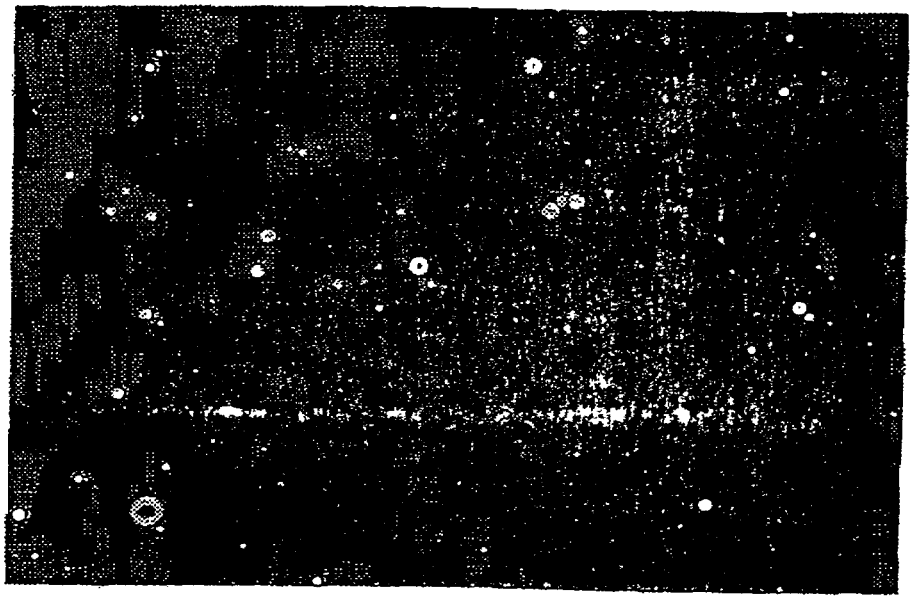
Figure 15:
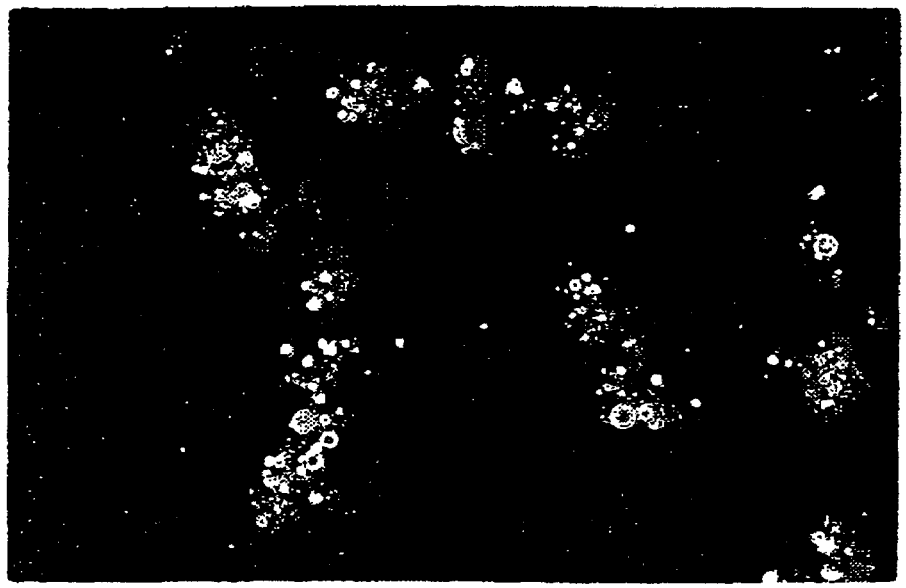
FIG. 15 shows the result of lectin agglutination reaction test regarding the formulation of Reference 2.2 obtained by the improvement of the well-known preparation.
Figure 16:
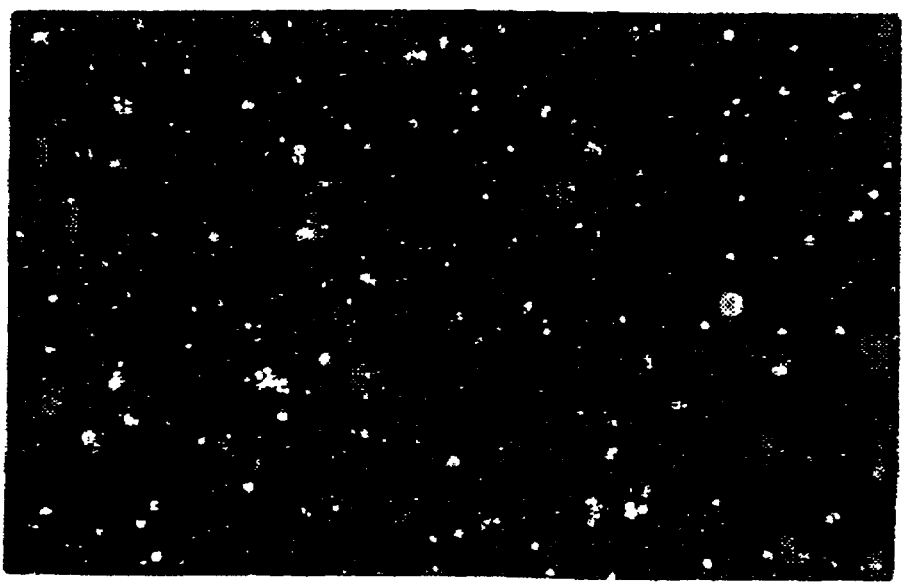
FIG. 16 shows the result of lectin agglutination reaction test regarding the formulation of Reference 2.1 obtained by the well-known preparation.

After preserved at 25 and 50° C. for one month, the lyophilized formulation obtained in Reference 1.1 was re-dispersed, and changes of average particle diameter and particle diameter distribution were examined. The result is as shown in Table 7, and FIG. 9.

TABLE 7

| | Average particle diameter (μm) | | |
|---|---|---|---|
| Preservation temperature | Before lyophilization | Immediately after lyophilization | 1 M |
| 25° C. | 2.6 | 2.8 | 1.9 |
| 50° C. | 2.6 | 2.8 | 1.4 |

The formulation containing a sugar alcohol, mannitol, which has been described as a stabilizer in the prior article (Japanese Patent Publication No. 1291/1988), demonstrated significant changes of the average particle diameter and particle diameter distribution at both temperatures of 25 and 50° C., one month later.

Test Example 1.5

Anti-Tumor Activity Examination

Guinea pig tumor Line 10 hepatoma cells were passaged in the peritoneal cavity of strain 2 line guinea pig. The $11^{th}$ day after the transplantation to the cavity, the ascites was taken from the guinea pig, and was suspended in HBSS at a cellular concentration of $2\times10^7$ cells/ml.

To the BCG-CWS lyophilized formulation obtained in Example 1.3 and a vehicle in the vial, 5 ml of injectable distilled water was added, and then, immediately, the vial was vigorously shaken for about 30 seconds, thus conducting the reconstitution. One ml aliquot of the content in the vial is portioned into a cryovial, and 1 ml of 1% w/w Polysorbate 80 was added thereto to render it an isotonic solution. Each 0.8 ml of the BCG-CWS formulation and the vehicle, and 0.4 ml of Line 10 tumor cells were combined together, and the combination was incubated at 37° C. for ten minutes.

On groups consisting of five guinea pigs, the clipper was used to remove the hair at the ventral part of each animals, and 150 μL of the mixture of tumor cells and the BCG-CWS formulation was subcutaneously transplanted to the animals ventral part using the 26 G needle and 1 ml syringe. The 150 μL aliquot contained $1\times10^6$ of the tumor cells, and 18.5 μg of the BCG-CWS as an agent.

Anti-tumor activity of the BCG-CWS was examined on the basis of inhibitory effect of the BCG-CWS on establishment of the tumor 35 days after the tumor transplantation. As the result, all animals in the group receiving the mixture of HBSS, the vehicle and the tumor cell suspension demonstrated the establishment of the tumor, whereas three of the five animals in the group receiving the BCG-CWS formulation demonstrated the inhibitory effect on establishment of the tumor.

TABLE 8

Inhibitory effect of BCG-CWS on establishment of Line 10 hepatoma

| Treatment | number inhibited the establishment number of one group |
|---|---|
| HBSS | 0/5 |
| Vehicle | 0/5 |
| BCG-CWS | 3/5 |

The lyophilized formulation provided according to the present invention is a stable formulation for a long period of time, and is capable to be reproduced into the oil-in-water emulsion having an anti-tumor activity by re-dispersion with a suitable dispersion solvent such as water. The lyophilized formulation of the present invention may be used depending on the efficacy of the bacterial component having anti-tumor activity, infection-preventing activity, and immunopotentiating activity, and used to potentiate the immunity of patients themselves. Consequently, the formulation can be used as medicaments, or prophylactics for treatment of cancers, infections, or the like.

Example 2.1

Dispersion-Aiding Solvent: Ethanol

Four milligrams of a BCG-CWS as a bacterial component was added to a mixture of 20 μL (0.5% w/w) of squalane and 4 ml of ethanol, and the resultant mixture was shaken or treated with ultrasonic at a room temperature to perform dispersion. Then, the dispersion was heated at 60° C. under a flow of nitrogen to evaporate the ethanol. After that, the residue that had been added with 4 mL of an aqueous solution of 0.2% w/w Polysorbate 80/5% mannit 1 was emulsified with a Potter-Elvehjem type homogenizer at about 1000 rpm/5 minutes, and the emulsion was heated for sterilization at 60° C. for 30 minutes, thereby obtaining an oil-in-water emulsion.

Example 2.2

Dispersion-Aiding Solvent: Toluene

According to a similar procedure to that of Example 2.1 except that toluene was used as a dispersion-aiding solvent instead of ethanol, a desired oil-in-water emulsion was obtained.

Reference 2.1 (the Well-Known Preparations: Cancer Research, 33, 2187-2195 (1973), etc.)

Four milligrams of a BCG-CWS as a bacterial component, and 20 μL (0.5% w/w) of squalane were poured into a Potter-Elvehjem type homogenizer, and the mixture was dispersed therein. Then, 4 ml of an aqueous solution of 0.2% w/w Polysorbate 80/5% mannitol was added thereto, and the mixture was emulsified with the same homogenizer, followed by heating the emulsion at 60° C. for 30 minutes, to obtain an oil-in-water emulsion.

Reference 2.2 (Improvement of the Well-Known Preparations)

Four milligrams of a BCG-CWS as a bacterial component, and 2 ml of distilled water were poured into a Potter-Elvehjem type homogenizer, and the mixture was dispersed therein to prepare a dispersion containing the agent. Two ml of the dispersion, and 2 ml of a mannitol aqueous solution (10%) were mixed together, and 20 μL (0.5% w/w) of squalane was added to the mixture, followed by dispersing it with the same homogenizer. Then, 80 μL of a 10% Polysorbate 80 aqueous solution was added thereto, and the mixture was emulsified with the same homogenizer, followed by heating the emulsion at 60° C. for 30 minutes, to obtain an oil-in-water emulsion.

Reference 2.3 (the Well-Known Preparation without any Oil)

Four milligrams of a BCG-CWS as a bacterial component, and 4 ml of an aqueous solution of 0.2% w/w Polysorbate 80/5% mannitol were poured into a Potter-Elvehjem type homogenizer, and the mixture was dispersed, and emulsified therein. Then, the emulsion was heated at 60° C. for 30 minutes to sterilize the same, thus obtaining an oil-in-water emulsion.

Test Example 2.1 Biological Activity Test

The oil-in-water emulsions of Examples 2.1-2.2, and those of References 2.1-2.3 were compared in terms of biological activity by means of mouse tumor metastasis model system, and the change of the biological activity due to the difference of the preparation was examined.

Five BALB/C mice aged eight weeks were used as one group. Colon26-M3.1 tumor cells were administered to the tail vein of the mice at $2.5 \times 10^4$ cells/animal, and then, 24 hours after the administration, the formulations of Examples and References as a BCG-CWS were administered at 100 μg/200 μL/aminal. Two weeks later, thoracotomy was performed on the animals to remove their lungs, and then the metastatic focus in the lungs was counted, thus comparing with the counts of the untreated animals as a control. The result is shown in Table 9.

TABLE 9

| Formulation | Agglutination reaction with lectin | Inhibitory effect on mouse tumor metastasis (%) |
|---|---|---|
| Untreated | | 0 |
| Example 2.1 | -- | 56 |
| Example 2.2 | -- | 37 |
| Reference 2.1 | -- | 52 |
| Reference 2.2 | ++ | 0 |
| Reference 2.3 | ++ | 6 |

Note: in Table 9, -- shows that the reaction is negative, and ++ shows that the reaction is positive.

Test Example 2.2

Encapsulation Test of Bacterial Component in Oil

To 200 μL of the formulations obtained in Example 2.1 and 2.2 or the formulations obtained in References 2.1, 2.2, and 2.3 (a BCG-CWS concentration is 1 mg/mL), 50 μL of a concanavalin A solution (a concanavalin A concentration is 1 mg/mL: 0.2 mM) was added, and the mixture was maintained at 25° C. for 30 minutes or more. The reaction was observed with a phase-contrast microscope to examine whether or not the agglutination reaction is present. The result is shown in Table 9, and FIGS. 10-12, 15, and 16.

As shown in Table 9, and FIGS. 10-12, 15, and 16, the formulations obtained by the preparation of the present invention was demonstrated to have a biological activity equivalent to that of the formulations obtained by the well-known preparation.

Example 3.1

One hundred mg of a BCG-CWS as a bacterial component was added to a mixture of 400 mg of squalane and 30 ml of toluene, and the resultant mixture was shaken or treated with ultrasonic for two to five minutes to perform dispersion. Then, the dispersion was heated at 50° C. under a flow of nitrogen to evaporate the toluene. After that, 100 mL of a 0.02% w/w Polysorbate 80 aqueous solution was added to the residue, and the mixture was roughly emulsified at 65° C. for ten minutes at 7000 rpm with a IKA ULTRA-TURRAX® T-25 type homogenizer (S25KV-25F). Then, 600 μL of a 10% w/w Polysorbate 80 aqueous solution was added thereto, and the mixture was adequately emulsified at 65° C. for five minutes at 15000 rpm with a IKA ULTRA-TURRAX® T-25 type homogenizer. After these emulsifications, 1200 μL of a 10% w/w Polysorbate 80 aqueous solution was further added thereto, and the mixture was emulsified for ten seconds at 7000 rpm with a IKA ULTRA-TURRAX® T-25 type homogenizer to obtain an oil-in-water emulsion.

Example 3.2

Five hundreds mg of a BCG-CWS as a bacterial component was added to a mixture of 2 g of squalane and 50 ml of toluene, and the resultant mixture was shaken or treated with ultrasonic for two to five minutes to perform dispersion. Then, the dispersion was heated at 50° C. under a flow of nitrogen to evaporate the toluene. After that, 500 mL of a 0.02% w/w Polysorbate 80 aqueous solution was added to the residue, and the mixture was roughly emulsified at 65° C. for ten minutes at 7000 rpm with a IKA ULTRA-TURRAX® T-25 type homogenizer (S25KV-25F). Then, 3 mL of a 10% w/w Polysorbate 80 aqueous solution was added thereto, and the mixture was adequately emulsified at 65° C. for ten minutes at 15000 rpm with a IKA ULTRA-TURRAX® T-25 type homogenizer. After these emulsifications, 6 mL of a 10% w/w Polysorbate 80 aqueous solution was further added thereto, and the mixture was emulsified for five minutes at 15000 rpm with a IKA ULTRA-TURRAX® T-25 type homogenizer to obtain an oil-in-water emulsion.

Example 3.3

Five hundreds mg of a BCG-CWS as a bacterial component was added to a mixture of 20 g of squalane and 300 ml of toluene, and the resultant mixture was shaken or treated with ultrasonic for 15 minutes to perform dispersion. Then, the dispersion was heated at 60° C. under a flow of nitrogen to evaporate the toluene. After that, 900 mL of an aqueous solution of 0.02% w/w Polysorbate 80/10% glycine was added to the residue, and the mixture was roughly emulsified for ten minutes at 7000 rpm with a homomixer. Then, 17 mL of a 10% w/w Polysorbate 80 aqueous solution was added thereto, and the mixture was adequately emulsified for ten minutes at 12000 rpm. After these emulsifications, 83 mL of a 10% w/w Polysorbate 80 aqueous solution was further added thereto, and the mixture was emulsified for five minutes at 3000 rpm with a homomixer to obtain an oil-in-water emulsion.

Reference 3.1 (One-Step Emulsification, without any Dispersion Solvent)

Four mg of a BCG-CWS as a bacterial component and 20 μL (0.5% w/w) of squalane were poured into a Potter-Elvehjem type homogenizer, and the mixture was dispersed therein. Then, 4 mL of a 0.2% w/w Polysorbate 80 aqueous solution was added thereto, and the mixture was emulsified with the same homogenizer to obtain an oil-in-water emulsion.

Reference 3.2 (One-Step Emulsification, Dispersion Solvent: Toluene)

To 30 mL of toluene containing 400 mg of squalane, 100 mg of a BCG-CWS was added, and the mixture was treated with ultrasonic to perform dispersion. After removing the toluene under a flow of nitrogen, 100 mL of a 0.2% w/w Polysorbate 80 aqueous solution was added to the residue, and the mixture was emulsified at 70° C. for five minutes at 15000 rpm with an emulsifying device (using IKA T-25/ S25KV25F shaft) to obtain an oil-in-water emulsion.

Test Example 3.1

Incorporation Ratio of a BCG-CWS Agent into the Formulation

Each of 200 μL of the formulations of Example 3.1, and References 3.1 and 3.2 was taken into a test tube, 200 μL of a 5% phenol aqueous solution was added thereto, and the mixture was stirred. After adding 1 mL of concentrated sulfuric acid thereto, and stirring the mixture, the resultant mixture was allowed to stand at room temperature for 30 minutes or more, and each absorbance at 490 nm was determined. The amount of a BCG-CWS agent was calculated based on the absorbance value using the standard curve that had been created (Seikagaku Jikken Koza 4 Chemistry of glucide P.370, Methods in Enzymology, 8, 93).

The result is shown in Table 10

TABLE 10

| Preparation | Amount of the agent in the formulation (of loaded amount %) |
|---|---|
| Reference 3.1 | 49 |
| Reference 3.2 | 16 |
| Example 3.1 | 113 |
| Example 3.2 | 119 |

As shown in Table 10, it is understood that the agent is almost quantitatively incorporated into the formulation, which is obtained by the preparation of the present invention. As such, the process for preparation of the formulation of the present invention has been found to enable to inhibit the generation of any insoluble material during the preparation, and to lower a loss of the agent.

Test Example 3.2

Incorporation Ratio of a BCG-CWS Agent into the Formulation

According to the procedure of Test Example 3.1, incorporation ratio of a BCG-CWS agent into the formulation of Example 3.3 was determined. The result is that a percentage of the agent incorporated into the formulation against the loaded amount was 109%.

Test Example 3.3

Biological Activity Test

When oil-in-water emulsions obtained by re-dissolving the formulations of Examples 3.1-3.2, and those of References 3.1-3.2 are compared in terms of biological activity by means of mouse tumor metastasis model system, the change of the biological activity due to the difference of the preparation may be examined.

Five BALB/C mice aged eight weeks were used as one group. Colon26-M3.1 tumor cells were administered to the tail vein of the mice at $2.5 \times 10^4$ cells/animal, and, 24 hours later, the formulations of Examples and References as a BCG-CWS were administered at 100 μg/200 μL/aminal. Two weeks later, thoracotomy was performed on the animals to remove their lungs, and then the metastatic focus in the lungs was counted to make a comparison, thereby showing that all formulations of the present invention have the biological activity.

The process for preparation according to the present invention allows to maintain an effective immunopotentiating activity of the bacterial component, and to prepare formulations in a large scale. Immunotherapy has been recently reconsidered, and particularly, a sole therapy involving a BCG-CWS has been recognized to have a good efficiency. Under the circumstance, the process for preparation according to the present invention provide a formulation that retains an immunopotentiating activity useful as pharmaceutics for the first time.

The invention claimed is:

1. An oil-in-water emulsion comprising a Bacillus Calmette-Guerin cell wall skeleton encapsulated in an oil wherein the emulsion is dispersed without any visible crude particles and which have an average fine particle size in the range of 0.1 μm to 20 μm, is negative for agglutination reaction with lectin, and is obtained by the following steps:
    (a) stirring a mixture of a Bacillus Calmette-Guerin cell wall skeleton, an oil, and an organic solvent to disperse the Bacillus Calmette-Guerin cell wall skeleton in the mixture;
    (b) evaporating off the organic solvent to form an oil wherein the Bacillus Calmette-Guerin cell wall skeleton is homogeneously dispersed, or an oil droplet wherein the Bacillus Calmette-Guerin cell wall skeleton is encapsulated in the oil; and then,
    (c) adding an aqueous solution containing a surfactant thereto, and emulsifying the mixture.

2. The oil-in-water emulsion of claim 1, wherein the organic solvent is selected from the group consisting of an aromatic hydrocarbon, an aliphatic hydrocarbon, a halogenated hydrocarbon, a lower alcohol, an acetate, an ether and a ketone.

3. The oil-in-water emulsion of claim 1, wherein the organic solvent is ethanol or toluene.

4. The oil-in-water emulsion of claim 1 or 3, wherein the oil is squalane.

* * * * *